Aug. 20, 1974 W. A. WARRINER Plant Pat. 3,595
ROSE PLANT
Filed Feb. 14, 1973
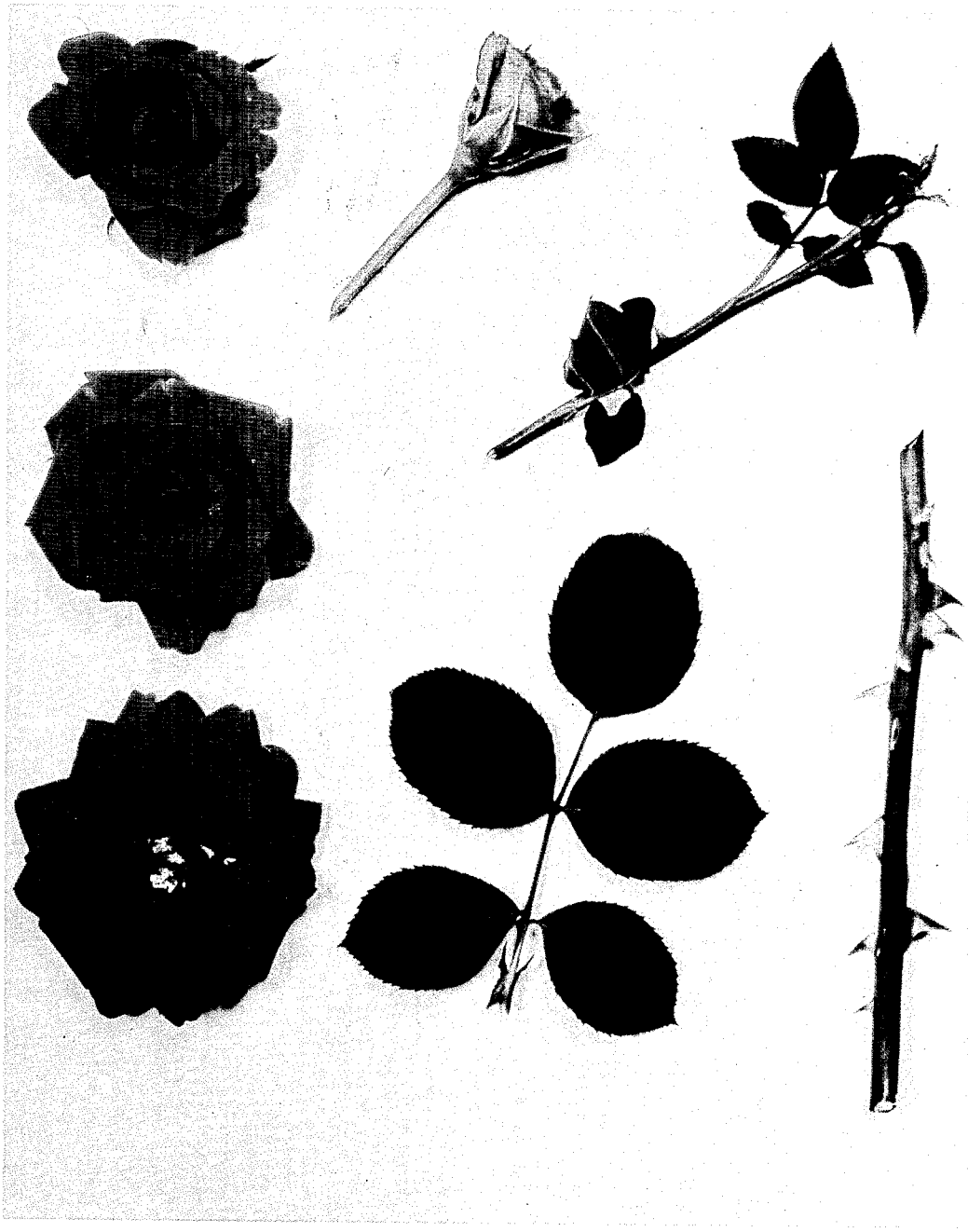

United States Patent Office

Plant Pat. 3,595

Patented Aug. 20, 1974

3,595

ROSE PLANT

William A. Warriner, Tustin, Calif., assignor to Jackson & Perkins Company, Medford, Oreg.

Filed Feb. 14, 1973, Ser. No. 332,255

Int. Cl. A01h 5/00

U.S. Cl. Plt.—29 1 Claim

The present invention relates to a new and distinct variety of rose plant of the floribunda class which was originated by me by crossing an unnamed seedling of Pink Peace × Happiness with pollen from an unnamed seedling whose parents were an unnamed seedling × Garnette.

The primary objective of this breeding was to produce a new red flowered rose variety of the floribunda class particularly suitable for use as a greenhouse cut flower.

This objective was substantially achieved along with other desirable improvements as evidenced by the following unique combination of characteristics which are outstanding in the new variety and which distinguish it from its parents as well as from all other varieties of which I am aware:

1. A vigorous habit of growth.
2. Stiff, erect stems.
3. Dark red buds near Wilson's Chrysanthemum crimson opening into lighter flowers of Wilson's Currant red.
4. Between 25–30 petals.
5. Very long vase life, lasting 10 days to 2 weeks as a cut flower after proper cooling.
6. A near immunity to rose powdery mildew.
7. Light, spicy fragrance.

This new variety is in some ways similar, but in no way genetically related to, the variety Mary DeVor, U.S. Plant Pat. No. 2,838. It is very much unlike all other varieties of which I am aware.

A. Buds are longer, more pointed than Mary DeVor.
B. Stems are thicker, stronger than Mary DeVor.
C. Has a much higher resistance to rose powdery mildew than Mary DeVor.
D. Open flowers of these two varieties are similar in color and form.

Asexual reproduction of this new variety by budding, as performed at Wasco, Calif., proves that the foregoing characteristics and distinctions reproduce true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
*Seed parent.*—Unnamed variety.
*Pollen parent.*—Unnamed variety.

Classification:
*Botanic.*—*Rosa hybrid.*
*Commercial.*—Floribunda.

FLOWER

Observations were made at Irvine, Calif., in early December, from plants in a greenhouse.

Blooming habit: Recurrent—continuous.
*Size.*—Approximately one inch when petals start to unfurl.
*Form.*—Long, pointed.
*Color.*—When sepals first divide near Chrysanthemum Crimson (824). When half blown; inside of petals near Currant Red (821), reverse of petals near Cardinal Red (822/1).
*Sepals.*—Color: Outer surface—Scheeles green (860/2). Few stipitate glands on outer surface of sepals. Inner surface—Scheeles green (860/2), covered with white tomentum. Three appendaged sepals lightly appendaged. Two unappendaged sepals hairy edged.
*Receptacle.*—Color: Scheeles green. Shape: Funnel. Size: Large, broad. Surface: Smooth.
*Peduncle.*—Length: Medium. Surface: Prickly on lower half. Color: Scheeles green (860/2). Strength: Stiff, erect.
*Opening.*—Outer petals slightly pointed; center petal tips curled back slightly.

Bloom:
*Size.*—Average size when fully expanded, 2¾ inches to 3 inches.
*Borne.*—Singly, in clusters. Clusters, flat.
*Stems.*—Medium, strong.
*Form.*—When first open, high center. Permanence—retains its form to the end.
*Petalage.*—Number of petals under normal conditions, 27–30.
*Color.*—Center of flower: Upper side of petals near Currant Red (821), generally a little darker. Reverse side of petals near Cardinal Red (822/1). Outer petals: Upper side of petals same as center petals. Reverse of petals same as center petals. Base of petals: Very small, near white base. General tonality from a distance Currant Red (821). No variegations.
*Discoloration.*—Very little fading occurs even after one week. Color does not "blue."
*Fragrance.*—Slight.

Petals:
*Texture.*—Thick, leathery.
*Surface.*—Inside—satiny. Reverse—satiny.
*Shape.*—Nearly round.
*Form.*—Tips slightly recurved; outer petals on the edges slightly quilled.
*Arrangement.*—Loosely imbricated.
*Petaloids in center.*—Few.
*Persistence.*—Drop off cleanly.
*Lastingness.*—On the plant—very long. As cut flower—very long.

Reproductive Parts:
*Stamens, anthers.*—Medium. Color—yellow. Arrangement—regular around styles.
*Stamens, filaments (threads).*—Short. Color—Rose red, except yellow at base.
*Pollen.*—Golden yellow.
*Styles.*—Loosely separated, of uneven lengths.
*Stigmas.*—Color—White.
*Ovaries.*—All enclosed in calyx.

Fruit: (Not observed).

PLANT

Form: Bush.
Growth: Very vigorous, upright, branching.
Foliage: Number of leaflets on normal mid-stem leaves, 5.
*Size.*—Medium.
*Quantity.*—Normal.
*Color.*—New foliage: Garnet Brown (00918/3). Old foliage: Parsley Green (00962), upper side Willow Green (between 000862 and 000862/1).

Leaflets:
*Shape.*—Broadly oval.
*Texture.*—Leathery. Under side—smooth. Ribs and veins—ordinary.
*Edge.*—Serrated, slightly undulated.

*Serration.*—Single, small.

*Petiole (rachis).* — Color — Green. Underside—prickles.

*Stipules.*—Medium, serrated.

*Disease resistance.*—Very resistant to mildew under normal growing conditions at Irvine, Calif.

Wood:

*New wood.*—Color—Light Green. Bark—Smooth.

*Old wood.*—Color.—Green. Bark—Smooth.

Prickles:

*Quantity.*—On main stalks—ordinary. On laterals—ordinary.

*Form.*—Narrow base, long, hooked slightly downward.

*Color.*—When young—Reddish at base, near Sap Green (62/2) at point.

*Position.*—Irregular.

Small Prickles:

*Quantity.*—On main stalks—very few. On laterals—very few.

*Color.*—Same as large prickles.

I claim:

1. A new and distinct variety of rose plant of the floribunda class, substantially as herein shown and described, characterized particularly as to novelty by the unique combination of its vigorous growth, dark red buds, currant red flowers, long vase life, resistance to rose powdery moldew, and broad oval leaflets.

No references cited.

ROBERT E. BAGWILL, Primary Examiner

UNITED STATES PATENT OFFICE
CERTIFICATE OF CORRECTION

Patent No. Plant Patent 3,595 Dated August 20, 1974

Inventor(s) William A. Warriner

It is certified that error appears in the above-identified patent and that said Letters Patent are hereby corrected as shown below:

Column 1, line 13, the comma should be a period.

Column 1, between lines 66 & 67 insert --Bud:--.

Column 4, line 13 "moldew" should be --mildew--.

Signed and sealed this 17th day of December 1974.

(SEAL)
Attest:

McCOY M. GIBSON JR.
Attesting Officer

C. MARSHALL DANN
Commissioner of Patents

USCOMM-DC 60376-P69
U.S. GOVERNMENT PRINTING OFFICE : 1969 O—366-334